United States Patent
Amano et al.

(10) Patent No.: US 7,094,926 B2
(45) Date of Patent: Aug. 22, 2006

(54) PROCESS FOR PRODUCING OPTICALLY ACTIVE CARBOXYLIC ACID SUBSTITUTED IN 2-POSITION

(75) Inventors: Susumu Amano, Kobe (JP); Masaru Mitsuda, Akashi (JP); Kenji Inoue, Kakogawa (JP); Koichi Kinoshita, Kakogawa (JP); Koki Yamashita, Kobe (JP); Yasuyoshi Ueda, Himeji (JP)

(73) Assignee: Kaneka Corporation, Osaka (JP)

( * ) Notice: Subject to any disclaimer, the term of this patent is extended or adjusted under 35 U.S.C. 154(b) by 13 days.

(21) Appl. No.: 10/182,260

(22) PCT Filed: Jan. 25, 2001

(86) PCT No.: PCT/JP01/00470

§ 371 (c)(1),
(2), (4) Date: Sep. 25, 2002

(87) PCT Pub. No.: WO01/55074

PCT Pub. Date: Aug. 2, 2001

(65) Prior Publication Data

US 2003/0144546 A1 Jul. 31, 2003

(30) Foreign Application Priority Data

Jan. 25, 2000 (JP) .............................. 2000-015432

(51) Int. Cl.
*C07C 51/58* (2006.01)
(52) U.S. Cl. ...................... 562/862; 562/602
(58) Field of Classification Search ............... 562/840, 562/858, 861, 864, 579, 602; 568/841
See application file for complete search history.

(56) References Cited

U.S. PATENT DOCUMENTS 2,786,045 A * 3/1957 Chirtel et al. ................ 528/271

FOREIGN PATENT DOCUMENTS

| EP | 110225 A1 | 6/1984 |
| EP | 159254 A1 | 10/1985 |
| EP | 0 599 444 A1 | 6/1994 |
| EP | 0 610 048 A2 | 8/1994 |
| EP | 0 747 392 A1 | 12/1996 |
| JP | 49-24914 A | 3/1974 |
| JP | 61-57534 | 3/1986 |
| JP | 64-79133 A | 3/1989 |
| JP | 64-79134 A | 3/1989 |
| JP | 9-295963 A | 11/1997 |
| JP | 10-7614 A | 1/1998 |
| JP | 10-310567 A | 11/1998 |
| JP | 11-192097 | 7/1999 |
| JP | 11-196889 | 7/1999 |

OTHER PUBLICATIONS

Hromatka et al., Monatshefte fuer Chemie (1957), 88, 234-41.*
Ege, Organic Chemistry, p. 562.*
Gisin et al, J. Am. Chem Soc. 91(10) 2691-5.*
Hegarty et al., Synthesis 1993; 1993: 606-610.*

* cited by examiner

*Primary Examiner*—Johann Richter
*Assistant Examiner*—Karl Puttlitz
(74) *Attorney, Agent, or Firm*—Sughrue Mion, PLLC

(57) ABSTRACT

A nitrous acid salt is added at a temperature of 10 to 80° C. to an aqueous solution which contains an optically active 2-aminocarboxylic acid (4) and a protonic acid, the amount of the latter acid being 1 to 3 equivalents to the former, and which has a proton concentration of 0.5 to 2 mol/kg to conduct a reaction to thereby produce an optically active 2-hydroxycarboxylic acid (1). Thionyl chloride and a basic compound are caused to act on the compound (1) to chlorinate it and simultaneously invert the configuration in the 2-position. Thus, an optically active 2-chlorocarboxylic acid chloride (5) is induced. The compound (5) is hydrolyzed to induce an optically active 2-chlorocarboxylic acid (2). The compound (2) is reacted with a thioacetic acid salt to incorporate an acetylthio group thereinto and simultaneously invert the configuration in the 2-position to thereby produce an optically active 2-acetylthiocarboxylic acid (3).

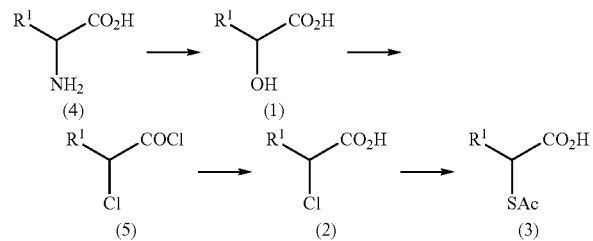

36 Claims, No Drawings

PROCESS FOR PRODUCING OPTICALLY ACTIVE CARBOXYLIC ACID SUBSTITUTED IN 2-POSITION

TECHNICAL FIELD

The present invention relates to a method of producing optically active 2-hydroxycarboxylic acids, optically active 2-chlorocarboxylic acids and optically active 2-acetylthiocarboxylic acids, which are important as intermediates for the production of pharmaceuticals and so forth.

BACKGROUND ART

Optically active 2-hydroxycarboxylic acids represented by the general formula (1):

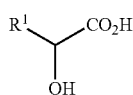
(1)

(wherein $R^1$ represents a substituted or unsubstituted alkyl group containing 1 to 12 carbon atoms, a substituted or unsubstituted aryl group containing 6 to 14 carbon atoms or a substituted or unsubstituted aralkyl group containing 7 to 15 carbon atoms) are important intermediates in the production of pharmaceuticals (for example, Biosci. Biotech. Biochem., 60 (8), 1279–1283, 1996) and, for the production thereof, the following methods are known, among others:

(i) L-Phenylalanine hydrochloride is prepared by treating L-phenylalanine with concentrated hydrochloric acid in chloroform and, then, (2S)-2-hydroxy-3-phenylpropionic acid is synthesized by treating an aqueous solution (proton concentration 1.4 mol/kg) containing L-phenylalanine and 4 equivalents, relative to L-phenylalanine, of a protonic acid (hydrochloric acid and sulfuric acid) with an aqueous solution containing 2 moles of sodium nitrite per mole of L-phenylalanine at 0° C. for 3 hours. After the reaction, the (2S)-2-hydroxy-3-phenylpropionic acid is recovered as crystals by ether extraction, dehydration, ether extract concentration and treatment of the residue with benzene (isolation yield 40%) (J. Amer. Chem. Soc., 86, 5326–5330, 1964);

(ii) (2S)-2-Hydroxy-3-phenylpropionic acid is synthesized by adding 4 moles, per mole of L-phenylalanine, of solid sodium nitrite to an aqueous solution (proton concentration 2.1 mol/kg) containing L-phenylalanine and 4 equivalents, relative to L-phenylalanine, of a protonic acid (sulfuric acid) at 0° C. over 5 hours, gradually warming the mixture to room temperature and stirring the same overnight. After the reaction, the (2S)-2-hydroxy-3-phenylpropionic acid is recovered as crystals by two or more times of extraction with ethyl acetate, washing of the extract with a saturated aqueous solution of sodium chloride, dehydration of the same over magnesium sulfate, concentration of the ethyl acetate solution and crystallization by addition of hexane (isolation yield 50%) (J. Heterocyclic Chem., 29, 431–438, 1992).

However, check experiments made by the present inventors concerning the above method (i) revealed that the method has such problems as the use of chloroform and benzene, which are highly toxic organic solvents, and the very low reaction yield (42%).

Checking of the above method (ii) by experiment revealed such problems as procedure complicatedness and increased capacity requirement, as resulting from the use of solid sodium nitrite and of large amounts of organic solvents and inorganic salts. It was also revealed that the reaction yield itself is low, namely 65%. In Biosci. Biotech. Biochem., 60 (8), 1279–1283, 1996, it is noted to the effect that the above method (ii) allows the formation, as a byproduct, of a large amount of a related substance (cinnamic acid) and accordingly gives a low yield, hence it is very difficult to employ that method on a commercial scale.

Further, it was revealed that the above methods (i) and (ii) still have another problem in that the optical purity is reduced by the formation of a considerable amount of the optical isomer (2R)-2-hydroxy-3-phenylpropionic acid as a byproduct as a result of racemization.

With such a background, alternative methods of producing optically active 2-hydroxy-3-phenylpropionic acid have been made, for example the method comprising asymmetric reduction of racemic 2-hydroxy-3-phenylpropionitrile using a microorganism (e.g. Biosci. Biotech, Biochem., 60 (8), 1279–1283, 1996 and JP-A 6-237789). These method are, however, not entirely favorable since the cyano compound to be used is highly toxic, the productivity is low and, further, no satisfactory optical purity can be obtained.

As for the production of optically active carboxylic acids substituted by a chlorine atom in the 2-position, which are represented by the general formula (2):

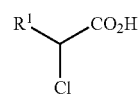
(2)

(wherein $R^1$ is as defined above) the following are known in the art:

(i) The method comprising using an amino acid as a starting material and chlorinating the same using sodium nitrite while retaining the configuration thereof (Liebigs Ann., 1907, 357, 1); and (ii) The method comprising chlorinating a 2-hydroxycarboxylic acid ester with configurational inversion (JP-A 61-57534).

However, the method (i) indeed gives a 2-chlorocarboxylic acid whose configuration at 2-position is (S) when a naturally occurring L-amino acid is used as the starting material but, for producing a 2-chlorocarboxylic acid whose configuration at 2-position is (R), it requires the use of a non-natural D amino acid, which is expensive, as the starting material, hence it has its limit as a method of producing (R)-2-chlorocarboxylic acids.

As for the method (ii), it is necessary to derivatize a 2-hydroxycarboxylic acid into a 2-hydroxycarboxylic acid ester, chlorinate the same with configurational inversion and then derivatize the chlorination product into a 2-chlorocarboxylic acid by hydrolysis. Thus, a number of steps have to be required and the method is not efficient.

Further, optically active 2-acetylthiocarboxylic acids represented by the general formula (3):

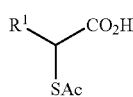

(wherein $R^1$ is as defined above) are important intermediates in the production of pharmaceuticals (e.g. as intermediates of antihypertensive agents; cf. JP-A 8-337527). For the production thereof, the following are known in the art:

(i) The method comprising thioacetylating a non-natural D-amino acid via configuration-retaining bromination (JP-A 8-337527 etc.);
(ii) The method comprising optical resolution of a racemic 2-acetylthiocarboxylic acid (JP-A 6-56790);
(iii) The method comprising hydrolyzing a thiazoline compound by means of a microorganism (JP-A 11-192097); and
(iv) The method comprising stereoseletively reducing a di-substituted acrylic acid derivative by means of a microorganism (JP-A 11-196889).

However, for producing an (S) form, the method (i) requires the use of an expensive non-natural D-amino acid as the starting material, hence it has its limit as a method of producing (S) forms.

The method (ii) lies in optical resolution of racemic 2-acetylthiocarboxylic acids, hence is not so efficient but has a problem from the industrial utilization viewpoint.

The method (iii) requires a separate procedure for increasing the optical purity since the 2-thiocarboxylic acid derivative obtained by hydrolysis of the thiohydantoin derivative has an optical purity as low as 82% ee. Thus it has a problem from the industrial utilization viewpoint.

The method (iv) is low in yield of asymmetric reduction of mercaptoacrylic acid derivative, namely 60 to 70% and, further, the 2-thiocarboxylic acid derivative obtained has an optical purity as low as 90% ee. Thus it has problems from the industrial utilization viewpoint.

DISCLOSURE OF INVENTION

In view of the above-mentioned state of the art, it is an object of the present invention to produce optically active 2-hydroxycarboxylic acids, which are important for the production of pharmaceuticals and other compounds, with good operability and in high yields.

In view of the above-mentioned state of the art, it is another object of the invention to isolate or purify optically active 2-hydroxycarboxylic acids expediently and efficiently on a commercial scale by efficiently removing related substances and/or undesired optical isomers coexisting with the desired optically active 2-hydroxycarboxylic acids.

In view of the above-mentioned state of the art, it is a further object of the invention to produce optically active 2-chlorocarboxylic acids, which are important for the production of pharmaceuticals and other compounds, from readily available starting materials, such as L-amino acids, efficiently and in high optical purity.

In view of the above-mentioned state of the art, it is a still further object of the invention to produce optically active 2-acetylthiocarboxylic acids, which are important for the production of pharmaceuticals and other compounds, from readily available starting materials, such as L-amino acids, efficiently and in high optical purity.

Thus, the present invention relates to a method of producing optically active 2-hydroxycarboxylic acids represented by the general formula (1):

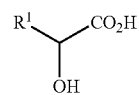

in which $R^1$ represents a substituted or unsubstituted alkyl group containing 1 to 12 carbon atoms, a substituted or unsubstituted aryl group containing 6 to 14 carbon atoms or a substituted or unsubstituted aralkyl group containing 7 to 15 carbon atoms, by reacting an optically active 2-aminocarboxylic acid represented by the general formula (4):

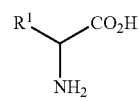

in which $R^1$ is as defined above, with a nitrite salt and a protonic acid in aqueous solution, which method comprises carrying out the reaction by adding the nitrite salt to an aqueous solution containing said optically active 2-aminocarboxylic acid and 1 to 3 equivalents, relative to the optically active 2-aminocarboxylic acid, of the protonic acid and having a proton concentration of 0.5 to 2 mol/kg at a temperature of 10 to 80° C.

The invention also relates to a method of crystallizing out optically active 2-hydroxycarboxylic acids which comprises causing crystallization of an optically active 2-hydroxycarboxylic acid represented by the above general formula (1) by using t-butyl methyl ether and a hydrocarbon solvent.

Further, the invention relates to a method of producing optically active 2-chlorocarboxylic acid chlorides represented by the general formula (5):

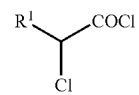

in which $R^1$ is as defined above, which comprises reacting an optically active 2-hydroxycarboxylic acid represented by the above general formula (1) with thionyl chloride and a basic compound for chlorination with inversion of the configuration at 2-position.

The invention also relates to a method of producing optically active 2-chlorocarboxylic acids represented by the general formula (2):

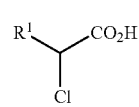

in which $R^1$ is as defined above, which comprises reacting an optically active 2-hydroxy-carboxylic acid represented by the above general formula (1) by reaction with thionyl chloride and a basic compound for chlorination with inversion of the configuration at 2-position and hydrolyzing the thus-obtained optically active 2-chloro-carboxylic acid chloride represented by the-general formula (5).

Furthermore, the present invention relates to a method of producing optically active 2-acetylthiocarboxylic acids represented by the general formula (3)

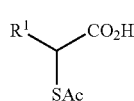
(3)

in which $R^1$ is as defined above, which comprises reacting an optically active 2-chlorocarboxylic acid represented by the general formula (2) with a thioacetate salt for substitution by acetylthio group with inversion of the configuration at 2-position.

In the following, the present invention is described in detail.

In the present specification, the following reactions (a) to (c) are included:
(a) The reaction which converts an optically active 2-aminocarboxylic acid of general formula (4) to the corresponding optically active 2-hydroxycarboxylic acid of general formula (1);
(b) The reaction which converts the optically active 2-hydroxycarboxylic acid (1) to the corresponding optically active 2-chlorocarboxylic acid chloride of general formula (5) and the reaction which converts the optically active 2-chlorocarboxylic acid chloride (5) to the corresponding optically active 2-chlorocarboxylic acid of general formula (2); and, further,
(c) The reaction which converts the optically active 2-chlorocarboxylic acid (2) to the corresponding optically active 2-acetylthiocarboxylic acid of general formula (3).

containing 6 to 14 carbon atoms or a substituted or unsubstituted aralkyl group containing 7 to 15 carbon atoms. Specifically, it includes, but is not limited to, methyl, ethyl, isopropyl, tert-butyl, n-octyl, hydroxymethyl, phenyl, p-hydroxyphenyl, benzyl, p-chlorobenzyl, p-fluorobenzyl and naphthyl group. Substituted or unsubstituted aralkyl groups containing 7 to 15 carbon atoms are preferred, and a benzyl group is more preferred.

As the substituent which the group $R^1$ may have, there may be mentioned alkoxy groups containing 1 to 12 carbon atoms, such as methoxy, ethoxy, t-butyloxy and n-octyloxy group, aryloxy groups containing 6 to 14 carbon atoms, such as phenyloxy and p-hydroxyphenyloxy group, aralkyloxy groups containing 7 to 15 carbon atoms, such as benzyloxy, p-chlorobenzyloxy and p-fluorobenzyloxy group, acyl groups containing 1 to 15 carbon atoms, such as acetyl and benzoyl group, a halogen atom and a hydroxyl group.

In cases where $R^1$ is an aryl or aralkyl group, the substituent on the phenyl group thereof is not particularly restricted but, as such, there may be mentioned, among others, halogen atoms such as fluorine and chlorine atoms, hydroxyl group, alkyl groups containing 1 to 12 carbon atoms, such as methyl and isopropyl group, aralkyl groups containing 7 to 15 carbon atoms, such as benzyl group, aryl groups containing 6 to 14 carbon atoms, such as phenyl group, alkoxy groups containing 1 to 12 carbon atoms, such as methoxy and isopropyloxy group, aralkyloxy groups containing 7 to 15 carbon atoms, such as benzyloxy group, aryloxy groups containing 6 to 14 carbon atoms, such as phenyloxy group, and acyl groups containing 1 to 15 carbon atoms, such as acetyl and benzoyl group. Among them, halogen atoms are preferably used. The position of such a substituent is not particularly restricted but the para position is usual. Although the phenyl group may have a plurality of such substituents as mentioned above, the phenyl group, when substituted, usually has one substituent.

When the optically active 2-aminocarboxylic acid (4) subjected to reaction (a) according to the invention is in (S) form, the (S) form of the optically active 2-hydroxycarboxylic acid (1) is predominant in the product obtained. When the optically active 2-aminocarboxylic acid (4) is in (R) form,

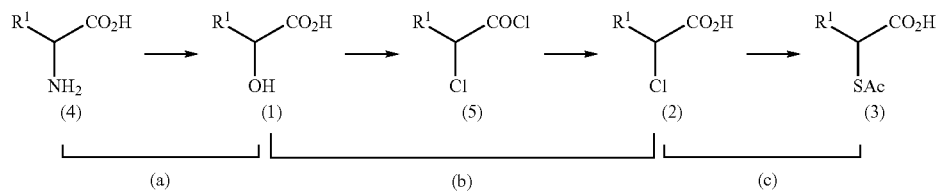

In addition, in the present specification, there is included a method of crystallizing out an optically active 2-hydroxycarboxylic acid represented by the general formula (1).

In the following, these reactions and method are described in detail one by one.

1. Reaction (a)

In the step of reaction (a) according to the invention, an optically active 2-hydroxycarboxylic acid (1) is synthesized by reacting an optically active 2-aminocarboxylic acid (4) with a nitrite salt and a protonic acid.

In the above general formula (4) or (1), R1 represents a substituted or unsubstituted alkyl group containing 1 to 12 carbon atoms, a substituted or unsubstituted aryl group the (R) form of the optically active 2-hydroxycarboxylic acid (1) is predominant in the product obtained.

The reaction (a) according to the invention is carried out in aqueous solution. While it is generally suitable to carry out the reaction in water, an organic solvent may coexist in an amount not producing any adverse effect.

The nitrite salt to be used in the reaction (a) according to the invention is not particularly restricted but includes, among others, alkali metal nitrites such as sodium nitrite, potassium nitrite, lithium nitrite and cesium nitrite. Sodium nitrite is preferred, however. It is particularly preferred to use the nitrite salt in the form of an aqueous solution (e.g. 20 to 40% (by weight) aqueous solution of sodium nitrite).

As the protonic acid to be used in the reaction (a) according to the invention, there may be mentioned, among others, inorganic acids, such as sulfuric acid, hydrochloric acid and nitric acid, and organic acids, such as acetic acid and citric acid. Generally, the use of inorganic acids is expedient and preferred and, for suppressing byproduct formation and attaining a high reaction yield, sulfuric acid is most preferred among others. The protonic acid can be used in the form of an aqueous solution.

The reaction (a) according to the invention is carried out by adding the above nitrite salt to an aqueous solution containing an optically active 2-aminocarboxylic acid (4) and a protonic acid.

On that occasion, the protonic acid is used in an amount of 1 to 3 equivalents, preferably 2 to 3 equivalents, relative to the optically active 2-aminocarboxylic acid (4). The proton concentration (normality) of the aqueous solution containing the optically active 2-aminocarboxylic acid (4) and the protonic acid is 0.5 to 2 mol/kg, preferably 1 to 2 mol/kg. When the amount and concentration of the protonic acid are insufficient, the optical purity of the desired product tends to decrease. When the amount and concentration of the protonic acid are excessive, the yield tends to decrease.

The proton concentration (normality) is expressed by the following formula 1:

Proton concentration (normality)=(Number of moles of protonic acid×number of ionic valency)/ (amount of water existing in reaction system) (mol/kg)

The number of ionic valency is the absolute value of the ionic valency of the protonic acid anion. Therefore, according to the above formula 1, the proton concentration (normality) of a solution containing 98 g (1 mol) of sulfuric acid per kg of water, for instance, is 2 mol/kg.

The nitrite salt is used in an amount of not less than 1 mole, preferably not less than 2 moles, judiciously 2 to 4 moles, per mole of the optically active 2-aminocarboxylic acid (4). The addition of the nitrite salt is preferably carried out continuously or in divided portions. In this case, the addition rate of the nitrite salt per hour is 0.2 to 1.5 moles, preferably 0.25 to 1.0 mole, more preferably 0.3 to 0.7 moles, per mole of the optically active 2-aminocarboxylic acid (4). Excessively high or low addition rates tend to result in decreased yields.

The nitrite salt addition and the subsequent reaction are carried out at 10 to 80° C., preferably 15 to 60° C., more preferably 20 to 50° C. At excessively low temperatures, the yield tends to decrease and/or the reaction mixture tends to solidify. At excessively high temperatures, the yield and optical purity tend to decrease.

The reactant concentrations depend on the optical active 2-aminocaboxylic acid (4) species and other factors, hence cannot be specified in all cases. As for the amount (weight) of the optically active 2-aminocarboxylic acid (4) used relative to the volume of the reaction mixture at the time of completion of the reaction, for instance, the lower limit is not less than 1% (w/v), preferably not less than 3% (w/v), and the upper limit is not more than 30% (w/v), preferably 20% (w/v). Generally, for example, 3 to 20% (w/v), more preferably 5 to 15% (w/v), in particular about 8±2% (w/v) is appropriate for carrying out the reaction.

The progress of the reaction can be followed by HPLC, for instance. Generally, the reaction will be complete in 24 hours after completion of the nitrite salt addition.

After completion of the reaction, the product can be recovered from the reaction mixture by ordinary work-up. For example, the reaction mixture after completion of the reaction is extracted with an ordinary extracting solvent, such as ethyl acetate, diethyl ether, methylene chloride, toluene or hexane. The desired product can be recovered from the thus-obtained extract by distilling off the reaction solvent and extracting solvent by such a procedure as heating under reduced pressure. Although the thus-obtained product is nearly pure, the purity may further be increased by ordinary purification procedures such as purification by crystallization, fractional distillation, column chromatography, etc.

By using the reaction (a) according to the present invention, it becomes possible to produce the desired product in very high reaction yield and optical purity.

2. Method of Crystallizing Out Optically Active 2-hydroxycarboxylic Acids (1)

In the process of producing the optically active 2-hydroxycarboxylic acid (1) by reacting the optically active 2-aminocarboxylic acid (4) with a nitrite salt and a protonic acid in aqueous solution, impurities, such as the corresponding α,β-unsaturated carboxylic acid (e.g. cinnamic acid, the phenyl group of which may be substituted) and like related substances as well as the undesired optical isomer are formed in many instances in addition to the desired 2-hydroxycarboxylic acid (1).

For removing these impurities and thereby isolating or purifying the above optically active 2-hydroxycarboxylic acid (1) expediently and efficiently, the crystallization method according to the invention is carried out using t-butyl methyl ether and a hydrocarbon solvent. The use of t-butyl methyl ether greatly contributes to improvements in yield and quality.

The above-mentioned hydrocarbon solvent may be an aliphatic hydrocarbon or an aromatic hydrocarbon. The aliphatic hydrocarbon is not particularly restricted but, for example, linear or cyclic aliphatic hydrocarbons containing 5 to 12 carbon atoms can suitably be used. As specific examples, there may be mentioned hexane, heptane, octane, decane, cyclohexane, methylcyclohexane, ethylcyclohexane and the like. Among them, hexane, heptane and methylcyclohexane are preferred. The aromatic hydrocarbon is not particularly restricted but monocyclic aromatic hydrocarbons containing 6 to 12 carbon atoms, for instance, can suitably be used. Specifically, there may be mentioned benzene, toluene, xylene and ethylbenzene. Among them, toluene is preferred. Form the crystallization yield viewpoint, aliphatic hydrocarbons are more preferably used. The hydrocarbon solvent may comprise either one single species or a combination of two or more species.

As for the quantity ratio between the above-mentioned hydrocarbon solvent and t-butyl methyl ether, the volume ratio of t-butyl methyl ether, relative to hydrocarbon solvent, is generally not more than 1, preferably not more than ⅔, still more preferably not more than ½, and generally not lower than 1/30, preferably not less than 1/20, still more preferably not less than 1/10. The ratio can appropriately be varied taking into consideration the solubility and treatment concentration of optically active 2-hydroxycarboxylic acid (1), the purification effect (impurity removing effect) and the physical properties of crystals to be recovered.

The technique of crystallization to be employed in carrying out the present invention is not particularly restricted but may comprise crystallization by cooling, crystallization by concentration, crystallization by solvent replacement (e.g. conversion of the solution comprising t-butyl methyl ether to a solution comprising the above hydrocarbon solvent), crystallization by addition of the above hydrocarbon solvent to the solution comprising t-butyl methyl ether, or crystallization by addition of the solution comprising t-butyl methyl ether to the above hydrocarbon solvent, for instance. Such techniques to be used in combination are also preferable.

Preferred among others are the technique comprising effecting crystallization by adding a hydrocarbon solvent to t-butyl methyl ether solution containing an optically active 2-hydroxycarboxylic acid (1), and the technique comprising effecting crystallization by adding t-butyl methyl ether solution containing an optically active 2-hydroxycarboxylic acid (1) to a hydrocarbon solvent. In particular, the technique comprising adding a hydrocarbon solvent to a t-butyl methyl ether solution containing an optically active 2-hydroxycarboxylic acid (1) for crystallization thereof is more preferably used.

Preferred as the optically active 2-hydroxycarboxylic acid (1) are those in which $R^1$ is a benzyl group, which may optionally have a substituent on the aromatic ring. Most preferred among others are optically active 2-hydroxy-3-phenylpropionic acid and optically active 2-hydroxy-3-(p-halophenyl)propionic acids.

The crystallization according to the present invention is judiciously carried out using the extract (inclusive of the one after washing) obtained, by using t-butyl methyl ether, from an aqueous solution containing the optically active 2-hydroxycarboxylic acid produced by the reaction mentioned above, or a concentrate of such extract.

The crystallization concentration is not particularly restricted but generally is 2 to 30% (w/v), preferably 5 to 20% (w/v), as expressed in terms of weight of optically active 2-hydroxycarboxylic acid (1) relative to volume of solvent.

The crystallization temperature is not particularly restricted but preferably is not lower than 30° C. from the viewpoint of physical properties and quality features of crystals to be obtained.

In carrying out the crystallization, seed crystals may be added according to need.

The crystal of optically active 2-hydroxycarboxylic acid (1) as formed by the crystallization method of the invention can be recovered by an ordinary solid-liquid separation technique such as centrifugation, pressure filtration or vacuum filtration. In the step of collecting crystal, the amount of crystal to be obtained can be maximized by cooling the solution for crystallization finally to a temperature of not higher than 10° C. The crystal obtained can further be dried according to need, for example by reduced pressure (vacuum) drying, to give dry crystals.

The crystallization method of the invention can also be utilized as a method of recrystallization or a method of isolation from the reaction mixture.

By using the crystallization method of the invention, it is possible to obtain the desired product in very high crystallization yield and with high quality.

3. Reaction (b)

The reaction (b) according to the invention includes the step of converting the optically active 2-hydroxycarboxylic acid represented by the above general formula (1) to the optically active 2-chlorocarboxylic acid chloride represented by the above general formula (5) by treatment with thionyl chloride and a basic compound for chlorination with inversion of the configuration at 2-position, and the step of converting, by hydrolysis, the optically active 2-chlorocarboxylic acid chloride (5) to the optically active 2-chlorocarboxylic acid represented by the above general formula (2).

In the general formula (1), (5) or (2) mentioned above, $R^1$ is as defined above. Benzyl is preferred, however.

In the reaction (b) according to the invention, inversion occurs of the configuration at 2-position in general formula (1). Thus, when the 2-position in the above general formula (1) has the configuration (S), the configuration at 2-position in the general formulas (5) and (2) is (R) and, when the 2-position in the general formula (1) has the configuration (R), the configuration at 2-position in the general formulas (5) and (2) is (S). The configuration at 2-position in general formula (1) maybe either (R) or (S). The configuration (S) is preferred, however.

The rate of inversion of configuration in the inverting chlorination reaction (b) according to the invention should preferably be not less than 95%. The rate of configurational inversion so referred to herein is expressed in terms of the ratio of the percentage of enantiomeric excess (% ee) of the product with inversed configuration [2-chlorocarboxylic acid chloride (5) or 2-chlorocarboxylic acid (2)] to the enantiomeric excess (% ee) of the starting material [2-hydroxycarboxylic acid (1)].

In the reaction (b) according to the invention, thionyl chloride is generally used in an amount of not less than 2 moles per mole of the optically active 2-hydroxycarboxylic acid (1). For suppressing the starting material or product from being decomposed or racemized and attaining a maximum yield, thionyl chloride is preferably used in further excess. Therefore, the amount of thionyl chloride to be used in the reaction (b) according to the invention is generally not less than 2 moles and, for maximizing the effects of the present invention, it is not less than 2.5 moles, preferably not less than 3 moles, per mole of the optically active 2-hydroxycarboxylic acid of general formula (1).

The basic compound to be used in the reaction (b) according to the invention is not particularly restricted but preferably is an organic base, an amide group-containing compound or a quaternary ammonium halide.

The above organic base includes alkylamines, aralkylamines, aryl amines and aromatic amines and, specifically, it includes, but is not limited to, triethylamine, tributylamine, ethyldiisopropylamine, N-methyl-2-pyrrolidine, dimethylaniline, imidazole, pyridine and lutidine. Preferred are triethylamine, diisopropylethylamine and pyridine.

The above amide group-containing compound specifically includes, but is not limited to, dimethylformamide, dimethylacetamide, tetramethylurea, N-methyl-2-pyrrolidone and hexamethylphosphoric triamide. Preferred are dimethylformamide and N-methyl-2-pyrrolidone.

The above quaternary ammonium halide specifically includes, but is not limited to, tetramethylammonium chloride, tetraethylammonium chloride, tetra-n-butylammonium chloride, benzyltrimethylammonium chloride, benzyltri-n-butylammonium chloride, tetramethylammonium bromide, tetraethylammonium bromide, tetra-n-butylammonium bromide, benzyltrimethylammonium bromide and benzyltri-n-butylammonium bromide. Preferred is tetra-n-butylammonium chloride.

Among the basic compounds mentioned above, amide group-containing compounds are generally preferred. Dimethylformamide, N-methyl-2-pyrrolidone and the like are particularly preferred.

In the reaction (b) according to the invention, the above basic compound may be used in a stoichiometric amount or in a larger amount relative to the optically active 2-hydroxycarboxylic acid of general formula (1) but, preferably, it is used in an amount not more than 0.5 mole per mole of acid (1). Usually, an amount of about 0.1 to 0.5 mole per mole of acid (1) is appropriate to the reaction.

The reaction solvent to be used in the reaction (b) according to the invention is preferably an aprotic organic solvent. The aprotic organic solvent is not particularly restricted but includes, among others, aliphatic hydrocarbon solvents such as n-hexane and methylcyclohexane; aromatic hydrocarbon solvents such as benzene, toluene and xylene; ether solvents such as diethyl ether, tetrahydrofuran, 1,4-dioxane, t-butyl methyl ether, dimethoxyethane and ethylene glycol dimethyl ether; halogenated hydrocarbon solvents such as methylene chloride, chloroform and 1,1,1-trichloroethane; and nitrogen-containing solvents such as acetonitrile, dimethylformamide, dimethylacetamide, diethylacetamide, dimethylbutyramide, N-methyl-2-pyrrolidone and hexamethylphosphoric triamide. These maybe used singly or two or more of them may be used in combination.

Particularly when an ether solvent such as diethyl ether, tetrahydrofuran, 1,4-dioxane, t-butyl methyl ether, dimethoxyethane or ethylene glycol dimethyl ether or an aromatic hydrocarbon solvent such as benzene, toluene or xylene is used, the reaction can proceed with high configurational inversion rate and high yield to give the optically active 2-chlorocarboxylic acid chloride (5) of high purity from the optically active 2-hydroxycarboxylic acid (1). Tetrahydrofuran, dimethoxyethane, 1, 4-dioxane and toluene are preferred among others, and tetrahydrofuran and toluene are particularly preferred.

The reaction temperature is preferably −20° C. to 120° C., more preferably 0° C. to 80° C., most preferably 20° C. to 60° C.

The reaction concentration is not particularly restricted but is not less than 5% (w/v), preferably not less than 10% (W/v), as expressed in terms of the amount of the optically active 2-hydroxycarboxylic acid of general formula (1) relative to the amount of the solvent.

The procedure for carrying out the reaction (b) according to the invention is not particularly restricted. For example, thionyl chloride is added to a solution of the optically active 2-hydoxycarboxylic acid (1), and the mixture is stirred for several hours. Thereafter, the above-mentioned basic compound is added and, then, the resulting mixture is stirred for several hours, whereby the optically active 2-chlorocarboxylic acid chloride (5) can be obtained. The optically active 2-chlorocarboxylic acid chloride (5) can be isolated, for example, by evaporating the solvent from the reaction mixture and then distilling the concentrate under reduced pressure.

Further, the optically active 2-chlorocarboxylic acid chloride (5) can be converted to the optically active 2-chlorocarboxylic acid (2) by hydrolysis.

Generally, the above hydrolysis reaction can be carried out by adding water at room temperature or at lower temperature to the reaction mixture containing, or a solution of, the optically active 2-chlorocarboxylic acid chloride (5) and stirring the mixture for several minutes to several hours.

The product can be recovered from this reaction mixture by ordinary work-up procedure. For example, the reaction mixture after completion of the hydrolysis reaction is extracted with an ordinary extracting solvent, such as ethyl acetate, diethyl ether, methylene chloride, toluene or hexane. The reaction solvent and extracting solvent are distilled off from the extract obtained by such a procedure as heating under reduced pressure, whereby the optically active 2-chlorocarboxylic acid (2) can be obtained.

It is also possible to once isolate the optically active 2-chlorocarboxylic acid chloride (5) by such a procedure as concentration or distillation without hydrolysis and then subjecting the chloride (5) to the hydrolysis reaction and subsequent procedure.

Furthermore, in extracting the optically active 2-chlorocarboxylic acid (2), a procedure may also be performed at least once which comprises distributing the optically active 2-chlorocarboxylic acid (2) in an aqueous phase under neutral to basic conditions to thereby remove impurities into an organic solvent. Moreover, a procedure may be performed which comprises distributing the optically active 2-chlorocarboxylic acid (2) into an organic solvent finally under acidic conditions to thereby remove impurities, inclusive of salts resulting from neutralization, into an aqueous phase. Although the thus-obtained product is nearly pure, the product can further be purified by an ordinary technique, such as purification by crystallization, fractional distillation or column chromatography, to further increase the purity.

4. Reaction (c)

In the step of reaction (c) according to the invention, the optically active 2-chlorocarboxylic acid represented by the above general formula (2) is reacted with a thioacetate salt for substitution by acetylthio group with inversion of the configuration at 2-position. Thus is prepared the corresponding optically active 2-acetylthiocarboxylic acid represented by the general formula (3).

In the general formula (2) or (3) mentioned above, $R^1$ is as defined hereinabove. Preferred is a benzyl group.

In the reaction (c) according to the invention, the configuration at 2-position in the general formula (2) is inverted. Namely, when the 2-position configuration in the above general formula (2) is (S), the 2-position configuration in general formula (3) is (R) and, when the 2-position configuration in general formula (2) is (R), the 2-position configuration in general formula (3) is (S). The 2-position configuration in general formula (2) may be either of (R) and (S) but preferably is (R).

In the reaction (c) according to the invention, the rate of configurational inversion is preferably not less than 95%. The rate of configurational inversion so referred to herein is expressed in terms of the ratio of the percentage of enantiomeric excess (% ee) of the product with inversed configuration [2-acetylthiocarboxylic acid (3)] to the enantiomeric excess (% ee) of the starting material [2-chlorocarboxylic acid (2)].

In the reaction (c) according to the invention, the thioacetate salt is not particularly restricted but includes salts of thioacetic acid with bases, preferably alkali metal thioacetates such as sodium thioacetate, potassium thioacetate, lithium thioacetate and cesium thioacetate. Among them, potassium thioacetate is preferably used.

Alternatively, the reaction may be carried out using thioacetic acid and a base (e.g. the hydroxide, hydride or alkoxide of an alkali metal) so as to prepare the corresponding thioacetate salt in the reaction system. The alkali metal hydroxide mentioned above includes, but is not limited to, lithium hydroxide, sodium hydroxide and potassium hydroxide. Among them, potassium hydroxide is preferred. The alkali metal hydride mentioned above includes, but is not limited to, lithium hydride, sodium hydride and potassium hydride. Among them, potassium hydride is preferred. The alkali metal alkoxide mentioned above includes, but is not limited to, lithium methoxide, sodium methoxide and potassium methoxide. Potassium methoxide is preferred, however.

In the reaction (c) according to the invention, the thioacetate salt is used in an amount of 1 to 5 equivalents, preferably 1 to 2 equivalents, relative to the optically active 2-chlorocarboxylic acid of general formula (2).

The reaction (c) according to the invention is preferably carried out in the presence of an aprotic polar solvent. The aprotic polar solvent is not particularly restricted but includes, among others, water-soluble ether compounds such as tetrahydrofuran, 1,4-dioxane, dimethoxyethane and ethylene glycol dimethyl ether; ester compounds such as ethyl acetate and butyl acetate; ketone compounds such as acetone and methyl ethyl ketone; halogenated compounds such as methylene chloride, chloroform and 1,1,1-trichloroethane; sulfur-containing compounds such as dimethyl sulfoxide; and nitrogen-containing compounds such as acetonitrile, dimethylformamide, dimethylacetamide, diethylacetamide, dimethylbutyramide, N-methyl-2-pyrrolidone and hexamethylphosphoric triamide. These may be used singly or two or more of them may be used in combination. Among them, water-soluble ether compounds, ester compounds, ketone compounds, sulfur-containing compounds and nitrogen-containing compounds are preferably used. More specifically, aprotic polar compounds having a dielectric constant of not less than 15 and a dipole moment of not less than 2.5 D are preferred. Suited for use among them are those nitrogen-containing compounds mentioned above which are liquid. From the viewpoint of reaction yield and rate of configurational inversion, amide group-containing liquid compounds are particularly preferred and, specifically, dimethylformamide, dimethylacetamide, diethylacetamide, dimethylbutyramide and N-methyl-2-pyrrolidone are preferred.

For causing such aprotic polar compounds to exist in the reaction system, one of such compounds which exists as a liquid may be used as the reaction solvent in the step of thioacetylation or one of such compounds which is a solid may be used in the form of a solution in water and/or another solvent such as mentioned below. Among the alternatives, the use as the reaction solvent is expedient. In cases where an aprotic polar solvent is used as the reaction solvent, the reaction solvent may comprise the aprotic polar compound alone or a mixed solvent composed of it and water and/or another organic solvent to be mentioned below.

The reaction solvent to be used in carrying out the reaction (c) according to the invention is generally water, an organic solvent or a mixture thereof. While the organic solvent includes the above-mentioned aprotic polar compounds, the other organic solvents are not particularly restricted but include, among others, alcohol solvents such as methanol, ethanol, butanol, isopropanol, ethylene glycol and methoxyalcohol; hydrocarbon solvents such as benzene, toluene, n-hexane and cyclohexane; and water-insoluble ether solvents such as diethyl ether, diisopropyl ether, dibutyl ether and t-butyl methyl ether. These may be used singly or two or more of them may be used in combination.

When the reaction yield is low with the solvent employed, a phase transfer catalyst may be used for improving the yield. The phase transfer catalyst to be used is not particularly restricted but includes, among others, crown ethers such as 12-crown-4,15-crown-5,18-crown-6,24-crown-8, dibenzo-18-crown-6, dibenzo-24-crown-8, dicyclohexyl-18-crown-6 and dicyclohexyl-24-crown-8; cryptands such as cryptand[2,2], cryptand[2,1,1], cryptand[2,2,1], cryptand [2,2,2] and cryptand[2B,2,2]; and quaternary ammonium salts such as trioctylmethylammonium chloride (trade name: ALIQUAT 336), trioctylmethylammonium bromide and methyltrialkyl ($C_8$ to $C_{10}$) ammonium chloride (trade name: Adogen 464). Among the phase transfer catalysts mentioned above, quaternary ammonium salts are generally preferred and, among them, trioctylmethylammonium chloride is judiciously used.

The level of addition of the phase transfer catalyst is not particularly restricted but, in general, it is preferably 0.05 to 5 mole percent, more preferably 0.3 to 1 mole percent, relative to the optically active 2-chlorocarboxylic acid of general formula (2).

The reaction temperature is preferably $-20°$ C. to $120°$ C., more preferably $0°$ C. to $50°$ C.

After completion of the reaction, the product can be recovered from the reaction mixture by ordinary work-up. For example, water is added to the reaction mixture after completion of the reaction and an extraction procedure is performed using an ordinary extracting solvent such as ethyl acetate, diethyl ether, methylene chloride, toluene or hexane. The reaction solvent and extracting solvent are distilled off, for example by heating under reduced pressure, whereby the product can be recovered. It is also possible to distill off the reaction solvent by heating under pressure, for instance, directly after completion of the reaction and then perform the same procedure as mentioned above. Although the thus-obtained product is nearly pure, the purity can be further increased by an ordinary purification procedure such as purification by crystallization, fractional distillation or column chromatography.

BEST MODES FOR CARRYING OUT THE INVENTION

The following examples illustrate the present invention in further detail. These examples are, however, by no means limitative of the scope of the present invention.

In the following, the assay of 2-hydroxy-3-phenylpropionic acid and the measurement of the apparent purity of 2-hydroxy-3-(p-fluorophenyl) propionic acid were carried out using the following analytical system. [Column: Develosil ODS-HG-3 (product of Nomura Chemical), 150 mm×4.6 mm I.D., mobile phase: 0.1% (wt/v) phosphoric acid water/acetonitrile=75/25, flow rate: 1.0 ml/min, detection: UV 210 nm, column temperature: $40°$ C., retention time: 2-hydroxy-3-phenylpropionic acid 3.9 min, 2-hydroxy-3-(p-fluorophenyl)propionic acid 5.1 min].

The above-mentioned apparent purity is expressed by the formula 2:

Apparent purity=(integrated area value for 2-hydroxy-3-(p-fluorophenyl)propionic acid/total integrated area value for all compounds detected)×100 (%)

The optical purity evaluation of 2-hydroxy-3-phenylpropionic acid and. 2-hydroxy-3-(p-fluorophenyl)propionic acid was made by derivatization into the corresponding methyl ester respectively by the method mentioned below.

Optical Purity Evaluation of 2-hydroxy-3-phenylpropionic Acid

The product (20 mg, 0.12 mmol) was dissolved in a mixed solvent composed of 1 ml of methanol and 3.5 ml of toluene, 166 mg (0.15 mmol) of a 10% solution of trimethylsilyldiazomethane was added dropwise, the reaction was allowed to proceed at room temperature for 30 minutes, the solvent was then distilled off under reduced pressure, and the concentrate was purified on a silica gel (hexane/ethyl acetate=4/1) to give methyl 2-hydroxy-3-phenylpropionate. This methyl ester was analyzed by HPLC [column: Chiralcel OD-H (product of Daicel Chemical Industries), mobile phase: hexane/isopropanol=98/2, flow rate: 1.0 ml/min, detection: UV 210 nm, column temperature: 5° C., retention time: S form 32 min, R form 30 min].

Optical Purity Evaluation of 2-hydroxy-3-(p-fluorophenyl) propionic Acid

The product (20 mg, 0.11 mmol) was dissolved in a mixed solvent composed of 1 ml of methanol and 3.5 ml of toluene, 166 mg (0.15 mmol) of a 10% solution of trimethylsilyl-diazomethane was added dropwise, the reaction was allowed to proceed at room temperature for 30 minutes, the solvent was then distilled off under reduced pressure, and the concentrate was purified on a silica gel (hexane/ethyl acetate=4/1) to give methyl 2-hydroxy-3-(p-fluorophenyl) propionate. This methyl ester was analyzed by HPLC [column: Chiralcel OJ (product of Daicel Chemical Industries), mobile phase: hexane/ethanol=95/5, flow rate: 1.0 ml/min, detection: UV 210 nm, column temperature: 20° C., retention time: R form 15 min, S form 16 min].

EXAMPLE 1

Production of (2S)-2-hydroxy-3-phenylpropionic Acid

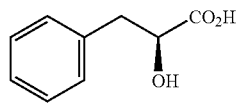

L-Phenylalanine (10.00 g, 60.5 mmol) was added to a dilution of 8.88 g (90.5 mmol) of concentrated sulfuric acid in 110 g of water and then, at an inside temperature of 20° C., a mixture of 10.45 g (151.5 mmol) of sodium nitrite and 20 g of water was added over 5 hours. After addition, the mixture was stirred at 20° C. for 20 hours, 100 ml of t-butyl methyl ether was then added and, after 30 minutes of stirring at 20° C., the organic phase was separated (extract 1). Further, 50 ml of t-butyl methyl ether was added to the aqueous phase, the mixture was stirred at 20° C. for 30 minutes, and the organic phase was separated (extract 2). The extracts 1 and 2 were combined. The combined extract (116.5 g) contained 8.6 g of (2S)-2-hydroxy-3-phenylpropionic acid (yield 86%, optical purity 95.9% ee). The proton concentration (normality) in the reaction of this example was 1.7 mol/kg, the amount of the protonic acid was 3.0 equivalents (relative to L-phenylalanine), and the reaction temperature was 20° C.

EXAMPLE 2

Production of (2S)-2-hydroxy-3-phenylpropionic Acid

L-Phenylalanine (10.00 g, 60.5 mmol) was added to a dilution of 5.93 g (60.5 mmol) of concentrated sulfuric acid in 110 g of water and then, at an inside temperature of 20° C., a mixture of 10.45 g (151.5 mmol) of sodium nitrite and 20 g of water was added over 5 hours. After addition, the mixture was further stirred at 20° C. for 20 hours and, thereafter, the same work-up procedure as in Example 1 was followed. The combined extract (116.1 g) obtained contained 8.7 g of (2S)-2-hydroxy-3-phenylpropionic acid (yield 87%, optical purity 95.2% ee). The proton concentration (normality) in the reaction of this example was 1.1 mol/kg, the amount of the protonic acid was 2.0 equivalents (relative to L-phenylalanine), and the reaction temperature was 20° C.

EXAMPLE 3

Production of (2S)-2-hydroxy-3-phenylpropionic Acid

L-Phenylalanine (10.00 g, 60.5 mmol) was added to a dilution of 4.15 g (42.4 mmol) of concentrated sulfuric acid in 110 g of water and then, at an inside temperature of 20° C., a mixture of 10.45 g (151.5 mmol) of sodium nitrite and 20 g of water was added over 5 hours. After addition, the mixture was further stirred at 20° C. for 20 hours and, thereafter, the same work-up procedure as in Example 1 was followed. The combined extract (115.8 g) obtained contained 8.7 g of (2S)-2-hydroxy-3-phenylpropionic acid (yield 87%, optical purity 92.0% ee). The proton concentration (normality) in the reaction of this example was 0.8 mol/kg, the amount of the protonic acid was 1.4 equivalents (relative to L-phenylalanine), and the reaction temperature was 20° C.

COMPARATIVE EXAMPLE 1

L-Phenylalanine (10.00 g, 60.5 mmol) was added to a dilution of 14.83 g (151.3 mmol) of concentrated sulfuric acid in 110 g of water and then, at an inside temperature of 20° C., a mixture of 10.45 g (151.5 mmol) of sodium nitrite and 20 g of water was added over 5 hours. After addition, the mixture was further stirred at 20° C. for 20 hours and, thereafter, the same work-up procedure as in Example 1 was followed. The combined extract (114.4 g) obtained contained 6.9 g of (2S)-2-hydroxy-3-phenylpropionic acid (yield 69%, optical purity 96.5% ee). The proton concentration (normality) in the reaction of this comparative example was 2.7 mol/kg, the amount of the protonic acid was 5.0 equivalents (relative to L-phenylalanine), and the reaction temperature was 20° C.

COMPARATIVE EXAMPLE 2

L-Phenylalanine (10.00 g, 60.5 mmol) was added to a dilution of 8.88 g (90.5 mmol) of concentrated sulfuric acid in 110 g of water and then, at an inside temperature of 0° C., a mixture of 10.45 g (151.5 mmol) of sodium nitrite and 20 g of water was added over 5 hours. After addition, the mixture was further stirred at 0° C. for 20 hours and, thereafter, the same work-up procedure as in Example 1 was followed. The combined extract (113.7 g) obtained contained 7.0 g of (2S)-2-hydroxy-3-phenylpropionic acid (yield 70%, optical purity 96.6% ee). The proton concentration (normality) in the reaction of this example was 1.7 mol/kg, the amount of the protonic acid was 3.0 equivalents (relative to L-phenylalanine) and the reaction temperature was 0° C.

COMPARATIVE EXAMPLE 3

A solution of 14 g (217 mmol) of sodium nitrite in 20 ml of water was added dropwise to a solution of 14 g (85 mmol) of L-phenylalanine in 100 ml of 1 N sulfuric acid at 0° C. over 3 hours, and the mixture was stirred overnight at room temperature. After extraction with three 100-ml portions of ethyl acetate, the organic phase was dried over sodium sulfate. The optical purity of (2S)-2-hydroxy-3-phenylpropionic acid in this extract was 93.0% ee. The solvent was distilled off under reduced pressure to give 12 g of crude (2S)-2-hydroxy-3-phenylpropionic acid. Further, this crude product was purified by recrystallization using 35 ml of ethyl acetate to give 7.5 g (yield 53%) of the desired (2S)-2-hydroxy-3-phenylpropionic acid. The proton concentration (normality) in the reaction of this comparative example was 1.0 mol/kg, the amount of the protonic acid was 1.2 equivalents (relative to L-phenylalanine), and the reaction temperature was 0° C. to room temperature.

$^1$H NMR (400 MHz, CDCl$_3$) δ (ppm): 7.34–7.25 (5H, m), 4.51 (1H, dd, J=7.3 Hz, 4.4 Hz), 3.21 (1H, dd, J=14.2 Hz, 4.4 Hz), 3.00 (1H, dd, J=13.7 Hz, 7.4 Hz).

EXAMPLE 4

Production of (2S)-2-hydroxy-3-phenylpropionic Acid

L-Phenylalanine (10.00 g, 60.5 mmol) was added to a dilution of 8.88 g (90.5 mmol) of concentrated sulfuric acid in 110 g of water and then, at an inside temperature of 40° C., a mixture of 10.45 g (151.5 mmol) of sodium nitrite and 20 g of water was added over 5 hours. After addition, the mixture was further stirred at 40° C. and, thereafter, the same work-up procedure as in Example 1 was followed. The combined extract (146.9 g) obtained contained 8.9 g of (2S)-2-hydroxy-3-phenylpropionic acid (yield 89%, optical purity 94.3% ee). The proton concentration (normality) in the reaction of this example was 1.7 mol/kg, the amount of the protonic acid was 3.0 equivalents (relative to L-phenylalanine), and the reaction temperature was 40° C.

EXAMPLE 5

Production of (2S)-2-hydroxy-3-phenylpropionic Acid

L-Phenylalanine (10.00 g, 60.5 mmol) was added to a dilution of 8.88 g (90.5 mmol) of concentrated sulfuric acid in 110 g of water and then, at an inside temperature of 70° C., a mixture of 10.45 g (151.5 mmol) of sodium nitrite and 20 g of water was added over 5 hours. After addition, the mixture was further stirred at 70° C. for 20 hours and, thereafter, the same work-up procedure as in Example 1 was followed. The combined extract (147.3 g) obtained contained 8.5 g of (2S)-2-hydroxy-3-phenylpropionic acid (yield 85%, optical purity 92.0% ee). The proton concentration (normality) in the reaction of this example was 1.7 mol/kg. The amount of the protonic acid was 3.0 equivalents (relative to L-phenylalanine) and the reaction temperature was 70° C.

EXAMPLE 6

Production of (2S)-2-hydroxy-3-phenylpropionic Acid

L-Phenylalanine (10.00 g, 60.5 mmol) was added to a dilution of 8.88 g (90.5 mmol) of concentrated sulfuric acid in 110 g of water and then, at an inside temperature of 20° C., a mixture of 10.45 g (151.5 mmol) of sodium nitrite and 20 g of water was added over 2 hours. After addition, the mixture was stirred at 20° C. for 20 hours and, thereafter, the same work-up procedure as in Example 1 was followed. The combined extract (116.3 g) obtained contained 8.5 g of (2S)-2-hydroxy-3-phenylpropionic acid (yield 85%, optical purity 94.0% ee). The proton concentration (normality) in the reaction of this example was 1.7 mol/kg. The amount of the protonic acid was 3.0 equivalents (relative to L-phenylalanine) and the reaction temperature was 20° C.

COMPARATIVE EXAMPLE 4

L-Phenylalanine (10.00 g, 60.5 mmol) was added to a dilution of 8.88 g (90.5 mmol) of concentrated sulfuric acid in 55 g of water and then, at an inside temperature of 20° C., a mixture of 10.45 g (151.5 mmol) of sodium nitrite and 20 g of water was added over 5 hours. After addition, the mixture was further stirred at 20° C. for 20 hours and, thereafter, the same work-up procedure as in Example 1 was followed. The combined extract (116.5 g) obtained contained 6.4 g of (2S)-2-hydroxy-3-phenylpropionic acid (yield 64%, optical purity 96.6% ee). The proton concentration (normality) in the reaction of this example was 3.3 mol/kg, the amount of the protonic acid was 3.0 equivalents (relative to L-phenylalanine), and the reaction temperature was 20° C.

COMPARATIVE EXAMPLE 5

This comparative example was to confirm the reaction results of the method described in J. Amer. Chem. Soc., 86, 5326–5330, 1964.

L-Phenylalanine hydrochloride (12.2 g, 60.5 mmol) was added to 183 ml of 5% sulfuric acid (sulfuric acid: 96.0 mmol) and the solution was treated with a mixture of 8.35 g (121 mmol) of sodium nitrite and 44.5 g of water at 0° C. for 3 hours. Thereafter, 100 ml of diethyl ether was added to the reaction mixture and, after stirring, the organic phase was separated (extract 1). Further, 50 ml of diethyl ether was added to the aqueous phase and, after stirring, the organic phase was separated (extract 2). The extracts 1 and 2 were combined. The combined extract (95.0 g) contained 4.2 g of (2S)-2-hydroxy-3-phenylpropionic acid (yield 42%, optical purity 92.6% ee). The proton concentration (normality) in the reaction of this comparative example was 1.4 mol/kg, the amount of the protonic acid was 4.0 equivalents (relative to L-phenylalanine), and the reaction temperature was 0° C.

COMPARATIVE EXAMPLE 6

This comparative example was to confirm the reaction results of the method described in J. Heterocyclic Chem., 29, 431–438, 1992.

Crystalline sodium nitrite (16.6 g, 241 mmol) was added to a mixture of 120 ml of 1 M sulfuric acid (sulfuric acid: 120 mmol) and 10.0 g (60.5 mmol) of L-phenylalanine at 0° C. over 5 hours. After addition, the temperature was raised to room temperature (15° C.), and the mixture was stirred overnight. Ethyl acetate (40 ml) was added to this reaction mixture and, after stirring, the organic phase was separated. The above procedure was further repeated twice. The organic phases were combined. The total extract (115.2 g) contained 6.6 g of (2S)-2-hydroxy-3-phenylpropionic acid (yield 66%, optical purity 96.2% ee). The proton concentration (normality) in the reaction of this comparative example was 2.1 mol/kg, the amount of the protonic acid was 4.0 equivalents (relative to L-phenylalanine), and the reaction temperature was 0° C. during the addition of sodium nitrite and room temperature (15° C.) after completion of the addition.

EXAMPLE 7

Crystallization of (2S)-2-hydroxy-3-phenylpropionic Acid

A portion of the (2S)-2-hydroxy-3-phenylpropionic acid/t-butyl methyl ether extract obtained in Example 2 (66.7 g, containing 5.0 g of (2S)-2-hydroxy-3-phenylpropionic acid, optical purity 95.2% ee) was concentrated under reduced pressure to give 20.0 g of a concentrate. While stirring this concentrate, 60 ml of hexane was gradually added at 40° C. to thereby cause precipitation of crystals. Then, the resulting mixture was cooled to 5° C. and further stirred for 2 hours. The crystals formed were filtered off under reduced pressure and then washed with two 10-ml portions of hexane/t-butyl methyl ether (75/25 by volume). The wet crystals obtained were dried under reduced pressure (vacuum) (full vacuum, 40° C., overnight) to give 4.5 g of (2S)-2-hydroxy-3-phenylpropionic acid (purity 98.7%, optical purity not lower than 99.9% ee, crystallization yield 89%).

EXAMPLE 8

Crystallization of (2S)-2-hydroxy-3-phenylpropionic Acid

A (2S)-2-hydroxy-3-phenylpropionic acid/t-butyl methyl ether extract separately obtained (3,450 g, containing 253.3 g of (2S)-2-hydroxy-3-phenylpropionic acid, optical purity 93.0% ee) was concentrated under reduced pressure to give 734 g of a concentrate. While stirring this concentrate, 2,230 ml of hexane was added over 3 hours at 40° C. to thereby cause precipitation of crystals. Then, the resulting mixture was cooled to 5° C. and further stirred for 2 hours. The crystals formed were filtered off under reduced pressure and then washed with two 250-ml portions of hexane/t-butyl methyl ether (75/25 by volume). The wet crystals obtained were dried under reduced pressure (vacuum) (full vacuum, 40° C., overnight) to give 232.2 g of (2S)-2-hydroxy-3-phenylpropionic acid (purity 98.2%, optical purity 99.8% ee, crystallization yield 90%).

COMPARATIVE EXAMPLE 7

A (2S)-2-hydroxy-3-phenylpropionic acid/ethyl acetate extract separately obtained (83.3 g, containing 5.0 g of (2S)-2-hydroxy-3-phenylpropionic acid, optical purity 93.7% ee) was concentrated under reduced pressure to give 20.0 g of a concentrate. While stirring this concentrate, 50 ml of hexane was gradually added at 40° C. to thereby cause precipitation of crystals. Then, the resulting mixture was cooled to 5° C. and further stirred for 2 hours. The crystals formed were filtered off under reduced pressure and then washed with two 10-ml portions of hexane/ethyl acetate (75/25 by volume). The wet crystals obtained were dried under reduced pressure (vacuum) (full vacuum, 40° C., overnight) to give 4.5 g of (2S)-2-hydroxy-3-phenylpropionic acid (purity 98.8%, optical purity 98.0% ee, crystallization yield 88%).

EXAMPLE 9

Crystallization of (2S)-2-hydroxy-3-phenylpropionic Acid

A (2S)-2-hydroxy-3-phenylpropionic acid/t-butyl methyl ether extract separately obtained (66.4 g, containing 5.0 g of (2S)-2-hydroxy-3-phenylpropionic acid, optical purity 95.3% ee) was concentrated under reduced pressure to give 16.7 g of a concentrate. While stirring this concentrate, 150 ml of toluene was gradually added at 40° C. to thereby cause precipitation of crystals. Then, the resulting mixture was cooled to 5° C. and further stirred for 2 hours. The crystals formed were filtered off under reduced pressure and then washed with two 10-ml portions of toluene/t-butyl methyl ether (90/10 by volume). The wet crystals obtained were dried under reduced pressure (vacuum) (full vacuum, 40° C., overnight) to give 4.0 g of (2S)-2-hydroxy-3-phenylpropionic acid (purity 99.2%, optical purity not lower than 99.9% ee, crystallization yield 80%).

EXAMPLE 10

Crystallization of (2R)-2-hydroxy-3-(p-fluorophenyl)propionic Acid

A mixture of 4.96 g of crude crystals of (2R)-2-hydroxy-3-(p-fluorophenyl)propionic acid (apparent purity 80%, optical purity 97.2% ee) and 10 ml of t-butyl methyl ether was slowly added to 40 ml of hexane containing 20 mg of seed crystals added, with stirring at 30° C. to thereby cause precipitation of crystals, and the mixture was then cooled to 5° C. and further stirred for 2 hours. The crystals formed were filtered off under reduced pressure and then washed with two 10-ml portions of hexane/t-butyl methyl ether (80/20 by volume) The wet crystals obtained were dried under reduced pressure (vacuum) (full vacuum, 40° C., overnight) to give 3.80 g of (R)-2-hydroxy-3-(p-fluorophenyl)propionic acid (apparent purity 99%, optical purity 99.9% ee, crystallization yield 95%).

EXAMPLE 11

(2R)-2-Chloro-3-phenylpropionic Acid Chloride

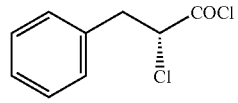

Toluene (50 ml) was added to 5.0 g (30.1 mmol) of (2S)-2-hydroxy-3-phenylpropionic acid, 10.7 g (90.3 mmol) of thionyl chloride was added dropwise, and the mixture was stirred at 40° C. for 2 hours. To the mixture was added 0.44 g (6.0 mmol) of dimethylformamide, and the resulting mixture was stirred at 40° C. for 24 hours. The reaction mixture was concentrated under reduced pressure, 90 ml of toluene was further added to the concentrate, and the dilution was again concentrated under reduced pressure. The thus-obtained concentrate was distilled under reduced pressure (boiling point: about 1 mmHg, 102–103° C.) to give 3.1 g (14.1 mmol, yield 47%) of (2R)-2-chloro-3-phenylpropionic acid chloride.

$^1$H NMR (400 MHz, CDCl$_3$) δ (ppm): 7.36–7.23 (5H, m), 4.71 (1H, t, J=7.3 Hz), 3.47 (1H, dd, J=14.2 Hz, 6.4 Hz), 3.02 (1H, dd, J=14.2 Hz, 7.8 Hz). $^{13}$C NMR (100 MHz. CDCl$_3$) δ (ppm): 170.25, 134.30, 129.36, 128.83, 127.84, 65.44, 40.68. IR (neat) (cm$^{-1}$): 3034, 1783, 1605, 1499, 1456, 1435, 1246, 1175, 1080, 1003, 925, 887, 835, 737, 698, 648, 548, 484.

EXAMPLE 12

(2R)-2-Chloro-3-phenylpropionic Acid

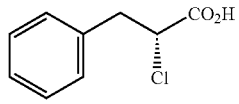

Thionyl chloride (0.66 ml, 9.0 mmol) was added dropwise to a solution of (2S)-2-hydroxy-3-phenylpropionic acid (500 mg, 3.0 mmol, optical purity 100% ee (S)) in 5 ml of tetrahydrofuran at room temperature, and the mixture was stirred for 15 hours. To the reaction mixture was added 170 mg (0.60 mmol) of tetra-n-butylammonium chloride, and the mixture was heated at 40° C. for 4 hours. Water (5 ml) was added to the reaction mixture and, after 30 minutes of stirring, the mixture was extracted with 90 ml of ethyl acetate. The organic phase was washed with 10 ml of a saturated aqueous solution of sodium chloride and then dried over anhydrous sodium sulfate. The solvent was distilled off under reduced pressure to give 499 mg (yield 90%) of the desired (2R)-chloro-3-phenylpropionic acid.

$^1$H NMR (400 MHz. CDCl$_3$) δ (ppm): 7.36–7.23 (5H, m), 4.49 (1H, t, J=7.3 Hz), 3.39 (1H, dd, J=14.1 Hz, 6.9 Hz), 3.02 (1H, dd, J=14.2 Hz, 7.8 Hz).

The optical purity of the product was determined by derivatization into the corresponding methyl ester by the following method. The product (25 mg, 0.14 mmol) was dissolved in a mixed solvent composed of 1 ml of methanol and 3.5 ml of toluene, 200 mg (0.18 mmol) of a 10% solution of trimethylsilyldiazomethane in hexane was added dropwise at room temperature and, after allowing the reaction to proceed at room temperature for 30 minutes, the solvents were distilled off under reduced pressure. The concentrate was purified on a silica gel column (hexane/ethyl acetate=4:1) to give methyl 2-chloro-3-phenylpropionate. This methyl ester was analyzed by HPLC [column: Chiralcel OD-H (product of Daicel Chemical Industries), eluent: hexane/isopropanol=100:1, flow rate: 1.0 ml/min, temperature: 40° C., detection wavelength: 210 nm, retention time: R form 26 min, S form 28 min] and found to have an optical purity of 98.9% ee (R) (rate of configurational inversion 98.9%).

EXAMPLE 13

(2R)-2-Chloro-3-phenylpropionic Acid

Thionyl chloride (43.8 g, 368.4 mmol) was added dropwise to a solution of 20.4 g (122.8 mmol) of (2S)-2-hydroxy-3-phenylpropionic acid (optical purity 100% ee (S)) in 200 ml of tetrahydrofuran, and the mixture was stirred at 35 to 40° C. for 2 hours. To that solution was added 1.8 g (24.6 mmol) of dimethylformamide, and the mixture was stirred at 42 to 44° C. for 6 hours. This reaction mixture was cooled and, while maintaining the temperature at 20° C., 70 ml of water was added dropwise and, after about an hour of stirring, the mixture was extracted with 200 ml of toluene. Water (70 ml) was added to the organic phase and, after pH adjustment to 9.0 with a 30% aqueous solution of sodium hydroxide, the organic phase was removed by phase separation. To the aqueous phase obtained was added 200 ml of toluene, the pH was adjusted to 1.0 with 35% aqueous hydrochloric acid, and the aqueous phase was removed by phase separation. The toluene was distilled off under reduced pressure from the thus-obtained toluene phase to give 21.1 g (114.3 mmol, yield 93%) of (2R)-2-chloro-3-phenylpropionic acid. The optical purity of the product as determined by the same method as in Example 12 was 99.8% ee (R) (rate of configurational inversion 99.8%).

EXAMPLE 14

(2R)-2-Chloro-3-phenylpropionic Acid 1,4-Dioxane (200 ml) was added to 20.4 g (122.8 mmol) of (2S)-2-hydroxy-3-phenylpropionic acid (optical purity 100% ee (S)), 43.8 g (368.4 mmol) of thionyl chloride was added dropwise, and the mixture was stirred at 40° C. for 2 hours. To that solution was added 1.8 g (24.6 mmol) of dimethylformamide, and the mixture was stirred at 40° C. for 6 hours. This reaction mixture was cooled and, while maintaining the temperature at 20° C., 70 ml of water was added dropwise and, after about an hour of stirring, the mixture was extracted with 200 ml of toluene. Water (70 ml) was added to the organic phase and, after pH adjustment to 9.0 with a 30% aqueous solution of sodium hydroxide, the organic phase was removed by phase separation. To the aqueous phase obtained was added 200 ml of toluene, the pH was adjusted to 1.0 with 35% aqueous hydrochloric acid, and the aqueous phase was removed by phase separation. The toluene was distilled off under reduced pressure from the thus-obtained toluene phase to give 19.1 g (103.3 mmol, yield 84%) of (2R)-2-chloro-3-phenylpropionic acid. The optical purity of the product as determined by the same method as in Example 12 was 99.7% ee (R) (rate of configurational inversion 99.7%).

EXAMPLE 15

(2R)-2-Chloro-3-phenylpropionic Acid

Thionyl chloride (43.8 g, 368.4 mmol) was added dropwise to a solution of 20.4 g (122.8 mmol) of (2S)-2-hydroxy-3-phenylpropionic acid (optical purity 100% ee (S)) in 200 ml of toluene, and the mixture was stirred at 40° C. for 2 hours. To that solution was added 1.8 g (24.6 mmol) of dimethylformamide, and the mixture was stirred at 40° C. for 24 hours. This reaction mixture was cooled and, while maintaining the temperature at 20° C., 70 ml of water was added dropwise and, after about an hour of stirring, extracted with 200 ml of toluene. Water (70 ml) was added to the organic phase and, after pH adjustment to 9.0 with a 30% aqueous solution of sodium hydroxide, the organic phase was removed by phase separation. To the aqueous phase obtained was added 200 ml of toluene, the pH was adjusted to 1.0 with 35% aqueous hydrochloric acid, and the aqueous phase was removed by phase separation. The toluene was distilled off under reduced pressure from the thus-obtained toluene phase to give 21.6 g (116.8 mmol, yield 95%) of (2R)-2-chloro-3-phenylpropionic acid. The optical purity of the product as determined by the same method as in Example 12 was 99.5% ee (R) (rate of configurational inversion 99.5%).

EXAMPLE 16

(2R)-2-Chloro-3-phenylpropionic Acid

Thionyl chloride (0.18 ml, 2.4 mmol) was added dropwise to a solution of 200 mg (1.2 mmol) of (2S)-2-hydroxy-3- phenylpropionic acid (optical purity 100% ee (S)) in 2 ml of dimethoxyethane at room temperature, and the mixture was stirred for 15 hours. To that reaction mixture was added 0.01 ml (0.12 mmol) of pyridine, and the mixture was stirred at 60° C. for 4 hours. Water (10 ml) was added to the reaction mixture and, after 30 minutes of stirring, the mixture was extracted with 50 ml of ethyl acetate. The organic phase was washed with 10 ml of a saturated aqueous solution of sodium chloride and dried over sodium sulfate. The solvent was distilled off under reduced pressure to give 135 mg (yield 61%) of the desired (2R)-2-chloro-3-phenylpropionic acid. The optical purity of the product as determined by the same method as in Example 12 was 97.6% ee (R) (rate of configurational inversion 97.6%).

EXAMPLE 17

(2R)-2-Chloro-3-phenylpropionic Acid

The reaction was carried out in the same manner as in Example 16 using 2 moles of thionyl chloride per mole of the starting material except that the solvents specified below in Table 1 were respectively used as the reaction solvent. The results obtained are shown below in Table 1.

TABLE 1

| Solvent | Yield (%) | Optical purity (% ee) | Configuration inversion rate (%) |
|---|---|---|---|
| THF | 35 | 99.4 | 99.4 |
| 1,4-Dioxane | 17 | 99.9 | 99.9 |
| Toluene | 23 | 72.6 | 72.6 |
| No solvent | 20 | 87 | 87 |

EXAMPLE 18

(2S)-2-Acetylthio-3-phenylpropionic Acid

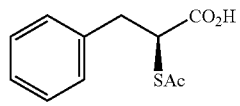

Potassium thioacetate (68 mg, 0.64 mmol) was added to a solution of 100 mg (0.54 mmol) of the (2R)-2-chloro-3-phenylpropionic acid obtained in Example 14 in 2 ml of dimethylformamide at room temperature, and the mixture was stirred for 24 hours. A 6% aqueous solution of sodium thiosulfate (0.5 ml) was added to the reaction mixture, and the whole mixture was extracted with 30 ml of ethyl acetate. The organic phase was washed with 3 ml of 6% sodium thiosulfate aqueous solution, 3 ml of water and 3 ml of a saturated aqueous solution of sodium chloride, and dried over sodium sulfate. The solvent was removed under reduced pressure to give 101 mg (yield 83%) of the desired (2S)-2-acetylthio-3-phenylpropionic acid.

$^1$H NMR (400 MHz. CDCl$_3$) δ (ppm): 7.34–7.22 (5H, m), 4.43 (1H, t, J=7.6 Hz), 3.30 (1H, dd, J=13.9 Hz, 7.9 Hz), 3.02 (1H, dd, J=13.9 Hz, 7.6 Hz), 2.33 (3H, s).

The optical purity of the product was determined by derivatization into the corresponding methyl ester by the following method. The product (25 mg, 0.12 mmol) was dissolved in a mixed solvent composed of 1 ml of methanol and 3.5 ml of toluene, 166 mg (0.15 mmol) of a 10% trimethylsilyldiazomethane solution in hexane was added dropwise. The reaction was allowed to proceed at room temperature for 30 minutes, the solvent was then distilled off under reduced pressure, and the concentrate was purified on a silica gel column (hexane/ethyl acetate=4:1) to give methyl 2-acetylthio-3-phenylpropionate. This methyl ester was analyzed by HPLC [column: Chiralcel OD-H (product of Daicel Chemical Industries), eluent: hexane/isopropanol=100:1, flow rate: 1.0 ml/min, temperature; 40° C., detection wavelength: 210 nm, retention time: R form 37 min, S form 38 min] and found to have an optical purity of 97.9% ee (S) (configurational inversion rate 98.2%).

EXAMPLE 19

(2S)-2-Acetylthio-3-phenylpropionic Acid

Potassium thioacetate (93 mg, 0.81 mmol) was added to a solution of 100 mg (0.54 mmol) of (2R)-2-chloro-3-phenylpropionic acid in 2 ml of N-methyl-2-pyrrolidone at room temperature, and the mixture was stirred for 24 hours. The work-up procedure in the same manner as in Example 18 of the reaction mixture was followed to give 114 mg (0.51 mmol, yield 94%) of the desired (2S)-2-acetylthio-3-phenylpropionic acid.

EXAMPLE 20

(2S)-2-Acetylthio-3-phenylpropionic Acid

The (2R)-2-chloro-3-phenylpropionic acid obtained in Example 13, 20.0 g (108.0 ml), to a mixture of 16.1 g (141.0 mmol) of potassium thioacetate and 40 ml of dimethylformamide was added dropwise at 0° C. and the mixture was stirred at room temperature for 24 hours. To the reaction mixture were added 60 ml of 6% sodium thiosulfate aqueous solution and 200 ml of toluene. The mixture was then adjusted to pH 1.7 with 35% aqueous hydrochloric acid and, after phase separation, the organic phase was recovered. This organic phase was washed with 60 ml of a 6% aqueous solution of sodium thiosulfate, 60 ml of a saturated aqueous solution of sodium chloride and 60 ml of water. The solvent was distilled off under reduced pressure to give 20.7 g (91.8 mmol, yield 85%) of the desired (2S)-2-acetylthio-3-phenylpropionic acid. The optical purity of the product as determined by the same method as in Example 18 was 98.9% ee (S) (configurational inversion rate 99.1%).

EXAMPLE 21

(2S)-2-Acetylthio-3-phenylpropionic Acid

The reaction was carried out in the same manner as in Example 18 except that the solvents specified below in Table 2 were respectively used as the reaction solvent. Based on the integrated area values obtained by HPLC analysis for (2S)-2-acetylthio-3-phenylpropionic acid (A) and (2R)-2-chloro-3-phenylpropionic acid (B) after the lapse of each time indicated in Table 2, the percentage of (2S)-2-acetylthio-3-phenylpropionic acid (A) as defined by the following formula 3 was calculated:

Percentage of A (%)=[(HPLC integrated area value for (A))(HPLC integrated area value for (B)+ HPLC integrated area value for (A))]×100

The results are shown below in Table 2. For evaluating the integrated values for the above compounds, the following system for HPLC analysis was used.

(HPLC)
[Column: Develosil ODS-HG-3 (product of Nomura Chemical), 150 mm×4.6 mm I.D., mobile phase: 0.1% (wt/v) phosphoric acid water/acetonitrile=75/25, flow rate: 1.0 ml/min, detection: UV 210 nm, column temperature: 40° C., retention time: (2R)-2-chloro-3-phenylpropionic acid (B) 19.9 min, (2S)-2-acetylthio-3-phenylpropionic acid (A) 22.6 min]

TABLE 2

| Solvent | After 3 hours | After 20 hours |
|---|---|---|
| Water | 1% | — |
| Methanol | 2% | — |
| Toluene | 0% | — |
| Ethyl acetate | 36% | 92% |
| t-butyl methyl ether | Reaction failed to proceed due to solidification | |
| Tetrahydrofuran | 32% | 93% |
| 1,4-Dioxane | 29% | 90% |
| Dimethoxyethane | 67% | 98% |
| Acetonitrile | 52% | 96% |
| Acetone | 79% | 97% |
| Dimethylformamide | 100% | — |
| N-Methyl-2-pyrrolidone | 100% | — |

EXAMPLE 22

(2S)-2-Acetylthio-3-phenylpropionic Acid

The reaction was carried out in the same manner as in Example 18 except that the solvents specified below in Table 3 were respectively used as the reaction solvent. After the lapse of the time indicated in Table 3, the percentage of (2S)-2-acetylthio-3-phenylpropionic acid as defined by the above formula 3 was calculated in the same manner as in Example 21.

TABLE 3

| Solvent | After 3 hours |
|---|---|
| Dimethylformamide:t-butyl methyl ether = 2:5 (by volume) | 97% |
| Dimethylformamide:ethyl acetate = 2:5 (by volume) | 93% |

INDUSTRIAL APPLICABILITY

The invention, which has the constitution mentioned above, makes it possible to produce optically active 2-hydroxycarboxylic acids, optically active 2-chlorocarboxylic acids and optically active 2-acetylthiocarboxylic acids, which are important in the production of pharmaceuticals and the like, from readily available starting materials with high optical purity and high efficiency. It also makes it possible to isolate or purify optically active 2-hydroxycarboxylic acids expediently and efficiently.

The invention claimed is:

1. A method of producing an optically active 2-chlorocarboxylic acid chloride represented by the general formula (5):

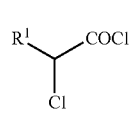
(5)

in which $R^1$ represents a substituted or unsubstituted aryl group containing 6 to 14 carbon atoms or a substituted or unsubstituted aralkyl group containing 7 to 15 carbon atoms, which comprises reacting an optically active 2-hydroxycarboxylic acid represented by the general formula (1):

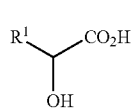
(1)

in which $R^1$ is as defined above, with thionyl chloride and an organic base for chlorination with inversion of the configuration at 2-position, wherein the rate of configurational inversion in the step of chlorination with inversion of configuration is not less than 95% wherein at least one solvent selected from among ether solvents is used as the reaction solvent for chlorination with inversion of configuration.

2. A method of producing an optically active 2-chlorocarboxylic acid represented by the general formula (2):

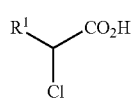
(2)

in which $R^1$ represents a substituted or unsubstituted aryl group containing 6 to 14 carbon atoms or a substituted or unsubstituted aralkyl group containing 7 to 15 carbon atoms, which comprises reacting an optically active 2-hydroxycarboxylic acid represented by the general formula (1):

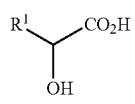
(1)

in which $R^1$ is as defined above, with thionyl chloride and an organic base for chlorination with inversion of the configuration at 2-position, wherein the rate of configurational inversion in the step of chlorination with inversion of configuration is not less than 95%, and hydrolyzing the thus-obtained optically active 2-chlorocarboxylic acid chloride represented by the general formula (5):

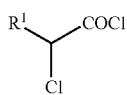

in which $R^1$ is as defined above wherein at least one solvent selected from among ether solvents is used as the reaction solvent for chlorination with inversion of configuration.

3. The method of production according to claim 1, wherein the configuration at 2-position in the optically active 2-hydrocarboxylic acid (1) is (S) and the configuration at 2-position in the optically active 2-chlorocarboxylic acid chloride (5) and in the optically active 2-chlorocarboxylic acid (2) is (R).

4. The method of production according to claim 1, wherein the configuration at 2-position in the optically active 2-hydrocarboxylic acid (1) is (R) and the configuration at 2-position in the optically active 2-chlorocarboxylic acid chloride (5) and in the optically active 2-chlorocarboxylic acid (2) is (S).

5. The method of production according to claim 1, wherein thionyl chloride is used in an amount of not less than 2 moles per mole of the optically active 2-hydroxycarboxylic acid (1).

6. The method of production according to claim 1, wherein at least one species selected from the group consisting of pyridine, triethylamine and diisopropylethylamine is used as the organic base.

7. A method of producing an optically active 2-chlorocarboxylic acid chloride represented by the general formula (5):

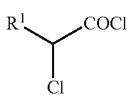

in which $R^1$ represents a substituted or unsubstituted alkyl group containing 1 to 12 carbon atoms, a substituted or unsubstituted aryl group containing 6 to 14 carbon atoms or a substituted or unsubstituted aralkyl group containing 7 to 15 carbon atoms, which comprises reacting an optically active 2-hydroxycarboxylic acid represented by the general formula (1):

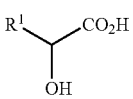

in which $R^1$ is as defined above,
with thionyl chloride and an amide group-containing compound for chlorination with inversion of the configuration at 2-position,
wherein the rate of configurational inversion in the step of chlorination with inversion of configuration is not less than 95%.

8. The method of production according to claim 7, wherein at least one of dimethylformamide and N-methyl-2-pyrrolidone is used as the amide group-containing compound.

9. A method of producing an optically active 2-chlorocarboxylic acid chloride represented by the general formula (5):

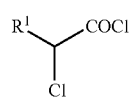

in which $R^1$ represents a substituted or unsubstituted alkyl group containing 1 to 12 carbon atoms, a substituted or unsubstituted aryl group containing 6 to 14 carbon atoms or a substituted or unsubstituted aralkyl group containing 7 to 15 carbon atoms,
which comprises reacting an optically active 2-hydroxycarboxylic acid represented by the general formula (1):

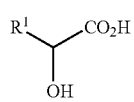

in which $R^1$ is as defined above, with thionyl chloride and a quaternary ammonium halide for chlorination with inversion of the configuration at 2-position,
wherein the rate of configurational inversion in the step of chlorination with inversion of configuration is not less than 95%.

10. The method of production according to claim 9, wherein tetra-n-butylammonium chloride is used as the quaternary ammonium halide.

11. The method of production according to claim 1, wherein the organic base is used in an amount of not more than 0.5 mole per mole of the optically active 2-hydroxycarboxylic acid (1).

12. The method of production according to claim 1, wherein the optically active 2-hydroxycarboxylic acid represented by the general formula (1) is obtained by reacting an optically active 2-aminocarboxylic acid represented by the general formula (4):

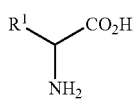

wherein $R^1$ is as defined above,
with a nitrite salt and a protonic acid for hydroxylation with retention of the configuration at 2-position.

13. The method of production according to claim 12, wherein sodium nitrite is used as the nitrite salt.

14. The method of production according to claim 12, wherein sulfuric acid is used as the protonic acid.

15. The method of production according to claim 1, wherein $R^1$ is a benzyl group.

16. The method of production according to claim 7, wherein a reaction solvent used in the reaction is an aprotic organic solvent.

17. The method of production according to claim 16, wherein the aprotic organic solvent is an ether solvent.

18. The method of production according to claim 2, wherein the configuration at 2-position in the optically active 2-hydrocarboxylic acid (1) is (S) and the configuration at 2-position in the optically active 2-chlorocarboxylic acid chloride (5) and in the optically acive 2-chlorocarboxylic acid (2) is (R).

19. The method of production according to claim 2, wherein the configuration at 2-position in the optically active 2-hydrocarboxylic acid (1) is (R) and the configuration at 2-position in the optically active 2-chlorocarboxylic acid chloride (5) and in the optically active 2-chlorocarboxylic acid (2) is (S).

20. The method of production according to claim 2, wherein thionyl chloride is used in an amount of not less than 2 moles per mole of the optically active 2-hydroxycarboxylic acid (1).

21. The method of production according to claim 2, wherein at least one selected from among ether solvents and aromatic hydrocarbon solvents is used as the reaction solvent for chlorination with inversion of configuration.

22. The method of production according to claim 21, wherein at least one species selected from the group consisting of tetrahydrofuran, dimethoxyethane, 1,4-dioxane and toluene is used as the reaction solvent for chlorination with inversion of configuration.

23. The method of production according to claim 2, wherein at least one species selected from the group consisting of pyridine, triethylamine and diisopropylethylamine is used as the organic base.

24. A method of producing an optically active 2-chlorocarboxylic acid represented by the general formula (2):

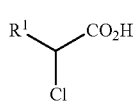

(2)

in which R¹ represents a substituted or unsubstituted alkyl group containing 1 to 12 carbon atoms, a substituted or unsubstituted aryl group containing 6 to 14 carbon atoms or a substituted or unsubstituted aralkyl group containing 7 to 15 carbon atoms, which comprises reacting an optically active 2-hydroxycarboxylic acid represented by the general formula (1):

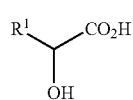

(1)

in which R¹ is as defined above, with thionyl chloride and an amide group-containing compound for chlorination with inversion of the configuration at 2-position, wherein the rate of configurational inversion in the step of chlorination with inversion of configuration is not less than 95%, and hydrolyzing the thus-obtained optically active 2-chlorocarboxylic acid chloride represented by the general formula (5):

(5)

in which R¹ is as defined above.

25. The method of production according to claim 24, wherein at least one of dimethylformamide and N-methyl-2-pyrrolidone is used as the amide group-containing compound.

26. A method of producing an optically active 2-chlorocarboxylic acid represented by the general formula (2):

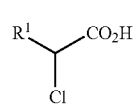

(2)

in which R¹ represents a substituted or unsubstituted alkyl group containing 1 to 12 carbon atoms, a substituted or unsubstituted aryl group containing 6 to 14 carbon atoms or a substituted or unsubstituted aralkyl group containing 7 to 15 carbon atoms, which comprises reacting an optically active 2-hydroxycarboxylic acid represented by the general formula (1):

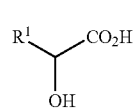

(1)

in which R¹ is as defined above, by reaction with thionyl chloride and a quaternary ammonium halide for chlorination with inversion of the configuration at 2-position, wherein the rate of configurational inversion in the step of chlorination with inversion of configuration is not less than 95%, and hydrolyzing the thus-obtained optically active 2-chlorocarboxylic acid chloride represented by the general formula (5):

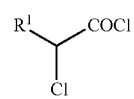

(5)

in which R¹ is as defined above.

27. The method of production according to claim 26, wherein tetra-n-butylammonium chloride is used as the quaternary ammonium halide.

28. The method of production according to claim 2, wherein the organic base is used in an amount of not more than 0.5 mole per mole of the optically active 2-hydroxycarboxylic acid (1).

29. The method of production according to claim 2, wherein the optically active 2-hydroxycarboxylic acid represented by the general formula (1) is obtained by reacting an optically active 2-aminocarboxylic acid represented by the general formula (4):

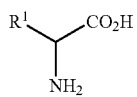

(4)

wherein R¹ is as defined above,
with a nitrite salt and a protonic acid for hydroxylation with retention of the configuration at 2-position.

30. The method of production according to claim 29, wherein sodium nitrite is used as the nitrite salt.

31. The method of production according to claim 29, wherein sulfuric acid is used as the protonic acid.

32. The method of production according to claim 2 wherein R¹ is a benzyl group.

33. The method of production according to claim 24, wherein a reaction solvent used in the reaction is an aprotic organic solvent.

34. The method of production according to claim 33, wherein the aprotic organic solvent is an ether solvent.

35. The method of production according to claim 1, wherein at least one solvent species selected from the group consisting of tetrahydrofuran, dimethoxyethane and 1,4-dioxane is used as the reaction solvent for chlorination with inversion of configuration.

36. The method of production according to claim 2, wherein at least one solvent species selected from the group consisting of tetrahydrofuran, dimethoxyethane and 1,4-dioxane is used as the reaction solvent for chlorination with inversion of configuration.

* * * * *

UNITED STATES PATENT AND TRADEMARK OFFICE
CERTIFICATE OF CORRECTION

| | | |
|---|---|---|
| PATENT NO. | : 7,094,926 B2 | Page 1 of 1 |
| APPLICATION NO. | : 10/182260 | |
| DATED | : August 22, 2006 | |
| INVENTOR(S) | : Susumu Amano et al. | |

It is certified that error appears in the above-identified patent and that said Letters Patent is hereby corrected as shown below:

On the face of the patent, under the heading "Foreign Application Priority Data", please insert the two priority applications which were not listed on the patent.

--May 30, 2000   (JP) ...................................2000-160937
  May 30, 2000   (JP) ...................................2000-160938 --

Signed and Sealed this

Twenty-sixth Day of June, 2007

JON W. DUDAS
*Director of the United States Patent and Trademark Office*